(12) United States Patent
Oki et al.

(10) Patent No.: US 7,972,277 B2
(45) Date of Patent: Jul. 5, 2011

(54) EXHALED BREATH ANALYSIS METHOD

(75) Inventors: Akio Oki, Kyoto (JP); Hiroaki Oka, Osaka (JP)

(73) Assignee: Panasonic Corporation, Osaka (JP)

( * ) Notice: Subject to any disclaimer, the term of this patent is extended or adjusted under 35 U.S.C. 154(b) by 181 days.

(21) Appl. No.: 12/434,324

(22) Filed: May 1, 2009

(65) Prior Publication Data

US 2009/0275852 A1 Nov. 5, 2009

Related U.S. Application Data

(63) Continuation of application No. PCT/JP2008/002945, filed on Oct. 17, 2008.

(30) Foreign Application Priority Data

| Oct. 29, 2007 | (JP) | 2007-279875 |
| Sep. 3, 2008 | (JP) | 2008-225521 |

(51) Int. Cl.
*A61B 5/08* (2006.01)
(52) U.S. Cl. ........................... 600/532; 600/529
(58) Field of Classification Search ........... 600/529–532
See application file for complete search history.

(56) References Cited

U.S. PATENT DOCUMENTS

| 6,350,609 B1 * | 2/2002 | Morozov et al. | 506/16 |
| 2004/0127808 A1 * | 7/2004 | Vaughan et al. | 600/532 |
| 2004/0210154 A1 | 10/2004 | Kline | |

FOREIGN PATENT DOCUMENTS

| JP | 2001-318069 | 11/2001 |
| JP | 2002-511792 | 4/2002 |
| JP | 2004-361160 | 12/2004 |
| JP | 2006-068711 | 3/2006 |
| JP | 2007-033388 | 2/2007 |
| JP | 3952052 | 5/2007 |

OTHER PUBLICATIONS

Phillips, M., et al., "Volatile organic compounds in breath as markers of lung cancer: a cross-sectional study", Early Report, The Lancet, Jun. 5, 1999, vol. 353, pp. 1930-1933.

(Continued)

*Primary Examiner* — Patricia C Mallari
*Assistant Examiner* — Michael D'Angelo
(74) *Attorney, Agent, or Firm* — McDermott Will & Emery LLP

(57) ABSTRACT

Handling of the condensate collecting vessel in conventional breath analysis apparatuses having a cold condensation mechanism is complicated, and time consuming.
The present invention provides a method for analyzing exhaled breath using a breath analysis apparatus, the breath analysis apparatus including: a vessel; an injection port of the exhaled breath; an outlet port of the exhaled breath; a cooling unit; an electrode zone; a counter electrode zone; and a chemical substance detection unit, in which the exhaled breath contains water vapor and a volatile organic compound, the volatile organic compound having a molecular weight of no lower than 15 and no higher than 500, and the method for exhaled breath analysis comprising the steps of: injecting the exhaled breath from the injection port into the vessel; condensing the exhaled breath on the outer peripheral surface of the electrode zone by cooling the electrode zone with the cooling unit; forming charged fine particles from the condensed breath; recovering the charged fine particles into the chemical substance detection unit by an electrostatic force; and detecting the volatile organic compound included in the charged fine particles recovered.

18 Claims, 12 Drawing Sheets

OTHER PUBLICATIONS

Phillips, M., "Method for the Collection and Assay of Volatile Organic Compound in Breath", Analytical Biochemistry 247, 1997, pp. 272-278, Academic Press.

Phillips, M., et al., "Prediction of Heart Transplant Rejection With a Breath Test for Markers of Oxidative Stress", The American Journal of Cardiology, Dec. 15, 2004, pp. 1593-1594, vol. 94, Excerpta Medica Inc.

Moser, B., et al., "Mass spectrometric profile of exhaled breath-field study by PTR-MS", Respiratory Physiology & Neurobiology 145, 2005, pp. 295-300, Elsevier, B.V.

The Lancet, vol. 353, Jun. 5, 1999, pp. 1897-1898.

* cited by examiner

EXHALED BREATH ANALYSIS METHOD

RELATED APPLICATIONS

This is a continuation of International Application No. PCT/JP2008/002945, with an international filing date of Oct. 17, 2008, which claims priority of Japanese Patent Application Nos. 2007-279875, filed on Oct. 29, 2007, and 2008-225521, filed on Sep. 3, 2008, the contents of which are hereby incorporated by reference.

BACKGROUND OF THE INVENTION

1. Field of the Invention

The present invention relates to a method for exhaled breath analysis in which a variety of components included in exhaled breath are concentrated by electrostatic atomization and analyzed.

2. Related Art

In exhaled breaths, water, nitrogen, oxygen and carbon dioxide, as well as metabolic components, and minor components such as volatile organic compounds and volatile sulfur compound are included. For example, alcohols, ketones, aldehydes, amines, aromatic hydrocarbons, fatty acids, isoprenes, mercaptans and the like, and derivatives thereof may be included.

Some correlations between a disease and the minor components included in the exhaled breath have been perceived. Research achievements suggesting the correlation between a disease and components in the exhaled breath have also been reported (Nonpatent Document 1, Nonpatent Document 2, Nonpatent Document 3, and Nonpatent Document 4). Unlike blood testing, the exhaled breath analysis enables examination without leading any physical and/or mental pain to the subjects, therefore, applications in the medical field such as diagnoses, follow up of postoperative course, decision of therapeutic strategies and the like are expected.

However, the concentration of the exhaled breath components suggested to correlate with a disease is extremely trace, which is generally at a level of from ppm to ppt (Nonpatent Document 4).

Thus, according to conventional breath analysis apparatuses, procedures in which the analysis efficiently performed by any of known techniques such as a method of cold condensation of exhaled breath, a method of capturing/concentrating the exhaled breath components to a trapping agent, or the like have been adopted.

For example, in a well-known method of cold condensation of the exhaled breath, a thermoelectric element is used (Patent Document 1). FIG. 11 shows an apparatus for cold condensation of exhaled breath disclosed in Patent Document 1.

In the apparatus for cold condensation of exhaled breath, the exhaled breath blown therein by a subject is cooled, and the condensate thereof is collected. The apparatus for cold condensation of exhaled breath includes breath passage tube 911, condensate collecting vessel 904, and thermoelectric element 903. The thermoelectric element 903 is connected to the condensate collecting vessel 904 via thermal conductor 902. The breath passage tube 911 and the condensate collecting vessel 904 are provided in an attachable/detachable manner. The breath passage tube 911 is provided with backflow prevention device 908 having two unidirectional valves, and is provided with flow meter 916 for measuring the volume of the exhaled breath blown into the apparatus.

The apparatus for cold condensation of exhaled breath shown in FIG. 11 is one of generally employed apparatuses since it can be handled comparably simply, although a long time period for obtaining the condensate in an amount needed for the analysis may be required.

As an alternative method, Patent Document 2 discloses an example of a concentration technique using electrospraying. This method executes concentration by electrospraying of a nonvolatile dilute biomolecule solution to volatilize the solvent in the mist, and thus can be used also in concentration of nonvolatile components included in the exhaled breath. Exemplary means for concentrating biological molecule solutions disclosed in Patent Document 2 is shown in FIG. 12.

By the electrospraying apparatus shown in FIG. 12, deposit of the nonvolatile substance including biomacromolecules is obtained. This deposit may be used for determining the interaction of the deposit of the nonvolatile substance with other substance. Further, Patent Document 2 discloses that the deposition of biological molecules by the electrospraying can be also utilized as means for microconcentration of dilute biomolecule solutions.

Nonpatent Document 1: THE LANCET Vol. 353, pp. 1930-1933 (1999)

Nonpatent Document 2: ANALYTICAL BIOCHEMISTRY Vol. 247, pp. 272-278 (1997)

Nonpatent Document 3: The American Journal of Cardiology pp. 1593-1594 (2004)

Nonpatent Document 4: Respiratory Physiology & Neurobiology Vol. 145, pp. 295-300 (2005)

Patent Document 1: Japanese Unexamined Patent Application, First Publication No. 2004-361160 (p. 6, FIG. 1)

Patent Document 2: Japanese Unexamined Patent Application, First Publication (translation of PCT Application) No. 2002-511792 (pp. 31, lines 12 to 13, p. 78, FIG. 9)

Patent Document 3: United States Patent Application, Publication No. 2004/0210154 (particularly, paragraph No. 0054)

Patent Document 4: Japanese Unexamined Patent Application, First Publication No. 2007-033388 (particularly, paragraph Nos. 0002 to 0005)

Patent Document 5: Japanese Patent No. 3952052

SUMMARY OF THE INVENTION

The conventional apparatuses disclosed in Patent Document 1 and Patent Document 2 both have a condensate reservoir vessel (condensate collecting vessel 904 in FIG. 11, and liquid vessel 1005 in FIG. 12), and a large quantity of the exhaled breath condensate must be reserved therein.

More specifically, in the example disclosed in Patent Document 1, condensate collecting vessel 904 having a volume of from 20 mL to 200 mL is cooled, and the droplet condensed on the vessel sidewall is fallen down to the bottom of the vessel and reserved.

Further, in the example disclosed in Patent Document 2, the vessel must be filled with a large quantity of the exhaled breath condensate such that the electrode can be soaked in the liquid enough for applying the voltage to the liquid in the vessel.

Such conventional techniques have been disadvantageous in that a considerable time period is required for obtaining such a large quantity of the exhaled breath condensate. Therefore, prompt analyses of the exhaled breaths on, for example, critical care patients in an emergency have been difficult.

In addition, necessity of collection of a large quantity of exhaled breath for obtaining the exhaled breath condensate in large quantities is also disadvantageous. Therefore, greater physical and/or mental strain has been imposed to users such as patients, elderly persons and infants, who are in weaker physical conditions as compared with healthy persons.

The present invention solves the foregoing problems in the prior art, and an object of the invention is to provide a method for analyzing exhaled breath through producing an exhaled breath condensate conveniently within a short period of time.

An aspect of the present invention which can solve the foregoing problems in the prior art is a method for analyzing exhaled breath using a breath analysis apparatus, the breath analysis apparatus including: a vessel; an injection port of the exhaled breath provided at one end of the vessel; an outlet port of the exhaled breath provided at the other end of the vessel; a cooling unit provided inside the vessel; an electrode zone provided in the vicinity of the cooling unit; a counter electrode zone provided inside the vessel; and a chemical substance detection unit provided in the vicinity of the counter electrode, wherein the exhaled breath contains water vapor and a volatile organic compound, and the method for exhaled breath analysis including the steps of: injecting the exhaled breath from the injection port into the vessel; condensing the exhaled breath on the outer peripheral surface of the electrode zone by cooling the electrode zone with the cooling unit; forming charged fine particles from the condensed breath; recovering the charged fine particles into the chemical substance detection unit by an electrostatic force; and detecting the volatile organic compound included in the charged fine particles recovered.

In the present invention, the volatile organic compound has a molecular weight of preferably no lower than 15 and no higher than 500.

In the present invention, the vessel is preferably closable.

In the present invention, the cooling unit is preferably a thermoelectric element.

In the present invention, the electrode zone is preferably cooled by the cooling unit to no higher than the dew condensation point of the water vapor.

In the present invention, the electrode zone and the cooling unit are preferably in contact either directly or via a thermal conductor.

In the present invention, it is preferred that the electrode zone be a cathode, and the counter electrode zone be an anode.

In the present invention, the charged fine particles preferably include water and the exhaled breath component.

In the present invention, the chemical substance detection unit preferably has a mechanism to remove the charge electrified by the charged fine particles.

In the present invention, the chemical substance detection unit is preferably ground.

In the present invention, the chemical substance detection unit is preferably separable from the vessel.

In the present invention, the step of forming the charged fine particles is preferably carried out by electrostatic atomization.

In the present invention, voltage application between the electrode zone and the counter electrode zone is preferably controlled depending on the electric current flowing between the electrode zone and the counter electrode zone in the step of forming the charged fine particles.

In the present invention, the voltage is preferably applied to the counter electrode toward the chemical substance detection unit in the recovery step.

In the present invention, the electrode zone is preferably heated for removing the chemical substance adhered to the electrode zone.

In the present invention, the thermoelectric element is preferably used for removing the chemical substance by heating the electrode zone.

In the present invention, the chemical substance adhered to the electrode zone is preferably removed with an airflow of a gas other than the exhaled breath.

The aforementioned and other objects, features, and advantages of the present invention are clarified by the following detailed description of preferred embodiments with reference to accompanying drawings.

According to the method for exhaled breath analysis of the present invention, an exhaled breath condensate can be produced on the outer peripheral surface of a cooled electrode zone within a short period of time. In addition, exhaled breath components can be efficiently collected into a chemical substance detection unit. As a result, it is advantageous in that the time period required for the analysis can be significantly shortened.

DETAILED DESCRIPTION OF THE INVENTION

Hereinafter, Embodiments of the present invention will be explained with reference to drawings.

Embodiment 1

Figure 1:
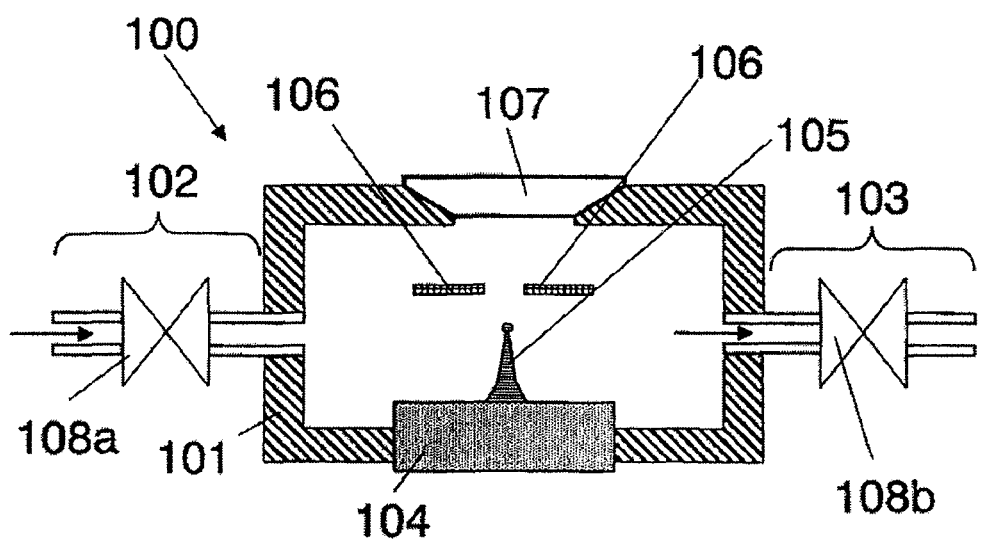
FIG. 1 shows a schematic view illustrating a breath analysis apparatus according to Embodiment 1 of the present invention.

FIG. 1 shows a schematic view illustrating a breath analysis apparatus according to Embodiment 1 of the present invention.

In this Embodiment, breath analysis apparatus 100 is constructed as in the following.

Vessel 101 is isolated from outside by a partition wall. Any substance migrates into and out from the outside through the partition wall. The vessel 101 may have a shape of rectangular box, or polyhedral, spindle, spherical or flow channel-like shape is also acceptable. It is preferred that the vessel 101 has a volume significantly small as compared with total inflow volume of the exhaled breath. For example, when the total inflow volume of the exhaled breath is 300 cc, the vessel has a volume of preferably no greater than 6 cc. It is desired that the material of the vessel 101 is accompanied by less adsorption gas or self-contaminating gas.

The material of the vessel 101 may be a metal such as stainless steel, aluminum or copper, or an inorganic substance such as quartz glass, borosilicate glass, silicon nitride, alumina or silicon carbide; or a silicon substrate having a thin film of an insulator such as silicon dioxide, silicon nitride or tantalum oxide formed on the surface thereof may be also used. Alternatively, two or more of these may be used in combination.

The material of the vessel 101 is preferably an acrylic resin, polyethylene terephthalate (PET), polyester, a fluorocarbon resin, PDMS, or the like. When the material of the vessel 101 is a plastic, it is more preferred that the inside wall of the vessel 101 is coated with a metal thin film. The metal thin film is most preferably an aluminum thin film since it is inexpensive and superior in gas barrier properties, however, other metal thin film may be also employed. Also, two or more of these may be used in combination. Although the vessel 101 is preferably rigid, it may be soft or flexible like an air bag, balloon, flexible tube, or syringe.

Injection port 102 is provided at one end of the vessel 101. The injection port 102 is used for injecting the exhaled breath into the vessel 101. The position at which the injection port 102 is provided may be selected ad libitum as long as it allows the exhaled breath to be quickly injected inside the vessel 101. For example, when the vessel 101 has a shape of a rectangular box, the injection port 102 is preferably positioned not at the corner but at central area of the face. In the present invention, the shape, the size, and the material of the injection port 102 are not particularly limited. The injection port 102 may be either a single tube as shown in FIG. 1, or may be branched along the path. Furthermore, the injection port 102 may be provided at one site, or at multiple sites.

Outlet port 103 is provided at the other end of the vessel 101. The outlet port 103 is used for discharging the excess exhaled breath from the vessel 101. The position at which the outlet port 103 is provided may be selected ad libitum as long as it enables the excess exhaled breath to be discharged from the vessel 101. In the present invention, the shape, the size, and the material of the outlet port 103 are not particularly limited. The outlet port 103 may be either a straight tube as shown in FIG. 1, or may be provided with a branched part along the path. Furthermore, the outlet port 103 may be provided at one site, or at multiple sites.

Cooling unit 104 is provided inside the vessel 101. Since cooling to no higher than the dew condensation point of the water vapor is permitted by providing the cooling unit 104, the water vapor and the volatile organic compound can be condensed. It is most preferred that the cooling unit 104 be a thermoelectric element. In addition, the cooling unit 104 may be a heat pipe in which a refrigerant such as water is used, an air heat-transfer element, or a cooling fan. In order to cool the exhaled breath efficiently, the surface area of the cooling unit 104 may be increased; the surface of the cooling unit 104 may be subjected to an emboss processing; or a porous structure may be provided on the surface of the cooling unit 104. It is most preferred that the position of the cooling unit 104 be on the bottom of the vessel 101. The position of the cooling unit 104 may be either on the lateral side or on the top side. Also, multiple cooling units 104 may be provided in combination of these alternatives.

In the embodiment of the present invention, when a thermoelectric element is used as the cooling unit 104, a radiating fin may be also provided at the radiating zone of the thermoelectric element. Alternatively, the radiating zone of the thermoelectric element may be water-cooled, air-cooled or cooled with another thermoelectric element, or other cooling means may be used. Also, two or more of these cooling methods may be employed in combination.

Electrode zone 105 is disposed inside the vessel 101, and provided in the vicinity of the cooling unit 104. The electrode zone 105 may be in direct contact with the cooling unit 104, or may be in contact via a thermal conductor such as a thermally conductive sheet, a thermally conductive resin, a metal plate, or grease.

It is preferred that the electrode zone 105 be cooled by the cooling unit to no higher than the dew condensation point of the water vapor 104. In general, the exhaled breath reportedly has a temperature of 34° C., and a humidity of 95%. In order to successively condense the water vapor and the volatile organic compound in the exhaled breath to permit dew formation, the temperature of the electrode zone 105 is preferably no lower than 0° C. and no higher than 30° C. The temperature of the electrode zone 105 is more preferably no lower than 0° C. and no higher than 15° C. The temperature of the electrode zone 105 is preferably uniform over the entire electrode zone 105, but may be nonuniform.

It is most preferred that the material of the electrode zone 105 be a metal. The material of the electrode zone 105 may be: a silicon or carbon nanotube; a carbon material such as graphite, fullerene, nanocone, carbon paste, or glassy carbon; or an organic conductive polymer such as PEDOT-PSS, pentacene, polyaniline, polyacetylene, or polypyrrole. Moreover, an inorganic conductive material such as tin oxide (ITO) or polysilicon, an organic metal such as organic silver, or other material which may be used as an emitter is also acceptable.

The electrode zone 105 may be provided either alone, or in plural numbers. The electrode zone 105 may be disposed unidimensionally, or along a straight line. The electrode 105 may be also disposed two-dimensionally such as circumferentially, parabolically, ellipsoidally, in a tetragonal lattice pattern, in an orthorhombic lattice pattern, in a closest packed lattice pattern, radially, or randomly. The electrode zone 105 may be also disposed three-dimensionally such as in a manner to form a spherical face, parabolically curved face, or elliptically curved face.

It is preferred that the electrode zone 105 has a needle-like shape. In order to cool the electrode zone 105 rapidly to no higher than the dew condensation point of the water vapor, the electrode zone 105 has a length of preferably no less than 3 mm and no greater than 10 mm. The material of the electrode zone 105 is preferably a material having superior thermal conduction, and most preferably a metal. Specifically, the material may be an elemental metal such as stainless steel, copper, brass, aluminum, nickel or tungsten, or may be an alloy or an intermetallic compound of combination of two or more of these. Furthermore, the surface of the electrode zone 105 may be covered with a thin film of a metal such as gold, platinum or aluminum.

The counter electrode zone 106 is provided so as to be opposed to the electrode zone 105. It is most preferred that the shape of the counter electrode zone 106 be circular. The counter electrode zone 106 may have a polygonal shape such as rectangle, or trapezoid. The material of the counter electrode zone 106 is preferably a metal. Specifically, the material may be an elemental metal such as stainless steel, copper, brass, aluminum, nickel or tungsten, or may be an alloy or an intermetallic compound of combination of two or more of these. Furthermore, the surface of the electrode zone 105 may be covered with a thin film of a metal such as gold, platinum or aluminum.

It is preferred that the electrode zone 105 be a cathode, and the counter electrode zone 106 be an anode. The voltage applied between the electrode zone 105 and the counter electrode zone 106 may be either fixed, or variable. The variable voltage is preferably controlled depending on the state of formation of the charged fine particles. The state of formation of the charged fine particles may be monitored by the electric current that flows between the electrode zone 105 and the counter electrode 106, or by the electric current that flows between the electrode zone 105 and the chemical substance detection unit 107. Alternatively, the electric current may be monitored by an exclusive electrode pair provided appropriately.

The chemical substance detection unit 107 is provided in the vicinity of the counter electrode zone 106. The chemical substance detection unit 107 may be a gas chromatograph, or other chemical substance detector may be also used. For example, MOSFET (metal-oxide semiconductor field effect transistor), ISFET (ion selective field effect transistor), a bipolar transistor, an organic thin film transistor, an optode, a metal oxide semiconductor sensor, a quartz crystal microbalance (QCM), a surface acoustic wave (SAW) element, a sensor such as a solid electrolyte gas sensor, an electrochemical battery sensor, a surface plasmon resonance (SPR) sensor or a Langmuir Blodgett membrane (LB membrane) sensor, or the like may be employed. The chemical substance detection unit 107 may be a high performance liquid chromatograph, a mass spectrometer, a nuclear magnetic resonance apparatus, or the like. The chemical substance detection unit 107 may be provided at one site as shown in FIG. 1, or at multiple sites. Moreover, when multiple chemical substance detection units are provided, they may be of a single type, or of different plural types.

In the embodiment of the present invention, as the chemical substance detection unit 107, a field effect transistor which is selectively sensitive to a chemical substance may be used. The field effect transistor may be produced using an inorganic semiconductor material such as silicon, gallium arsenide, carbon nanotube, or silicon nanowire. Alternatively, the field effect transistor may be produced using an organic semiconductor material such as pentacene, polythiophene, or PEDOT-PSS. The organic electrochemical transistor may be also produced using an organic semiconductor material. In the present invention, the material, the size, the number, and the method for production of the field effect transistor are not particularly limited.

It is preferred that the chemical substance detection unit 107 be subjected to static elimination. For example, when the exhaled breath is negatively charged, the chemical substance detection unit 107 is to be negatively charged. Since the operation of the chemical substance detection unit 107 is greatly affected when the charge intensity is in excess, to permit the static elimination is preferred. The static elimination may be carried out either constantly or arbitrarily.

It is preferred that the chemical substance detection unit 107 be subjected to the static elimination by grounding. The static elimination of the chemical substance detection unit 107 is preferably carried out by an ionizer.

The chemical substance detection unit 107 is preferably separable from the vessel 101. It is preferred that the chemical substance detection unit 107 be washed after the chemical substance detection unit 107 is separated. Also, the chemical substance detection unit 107 may be disposable because detection of the chemical substance can be performed in a clean state without being concerned about the previous measurement history.

The injection port 102 and the outlet port 103 are preferably provided with valve 108*a* and valve 108*b*. These valve 108*a* and 108*b* preferably make the vessel 101 closable. In the present invention, the material, the position, and the type of the valve 108*a* and 108*b* are not particularly limited. Further, the injection port 102 and outlet port 103 may have a low conductance.

In the embodiment of the present invention, the injection port 102 and the outlet port 103 may be provided with a control valve for controlling the flow of the exhaled breath. The control valve may be either a check valve, or a stop valve.

In the embodiment of the present invention, the injection port 102 and the outlet port 103 may be provided with a measuring instrument for measuring the flow rate of the exhaled breath. The measuring instrument may be an integrating flowmeter, a mass flow meter, or other flow instrument.

Figure 2:
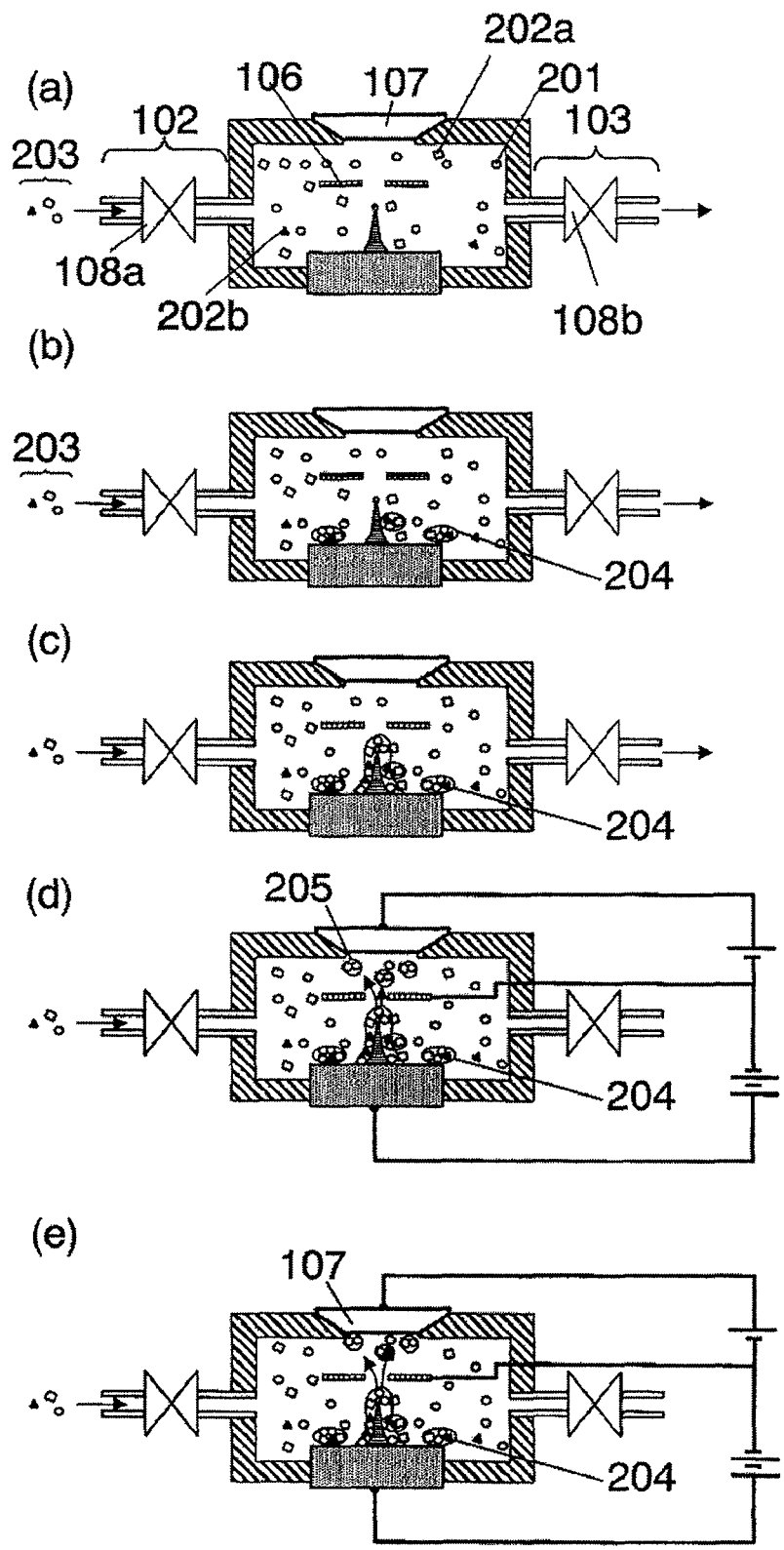
FIG. 2 shows an explanatory view illustrating the operation of the breath analysis apparatus according to Embodiment 1 of the present invention.

FIG. 2 shows an explanatory view illustrating the operation of the breath analysis apparatus according to Embodiment 1 of the present invention. In FIG. 2, the same constituting components as those shown in FIG. 1 are designated with the same reference signs, and their explanation is omitted.

In the injection step, exhaled breath 203 including water vapor 201 and exhaled breath components 202*a*, 202*b* is injected into the vessel 101 through the injection port 102. FIG. 2 (*a*) illustrates the injection step. In discriminating whether or not the vessel 101 is filled with the exhaled breath 203, the chemical substance detection unit 107 may be used, or any chemical substance detection unit other than the chemical substance detection unit 107 may be used. The chemical substance detection unit 107 may be provided either alone, or in plural numbers.

In the injection step, it is preferred to execute the injection with compression from the side of the injection port 102, or the injection with depressurization on the side of the outlet port 103 is also acceptable.

In the injection step, when the compression from the side of the injection port 102 is conducted, an electric pump such as a diaphragm pump, a peristaltic pump or a syringe pump may be used for the injection, or a syringe or a dropping pipette may be used for manual injection. Alternatively, the expired breath may be directly injected.

In the injection step, when depressurization on the side of the outlet port 103 is conducted, a diaphragm pump, a peristaltic pump, a syringe pump or an electric pump may be used for the injection. Alternatively, a syringe may be used for manual injection.

In the injection step, filling the vessel 101 with clean air before the exhaled breath 203 is injected into the vessel 101 is preferred. The vessel 101 may be filled with dry nitrogen or any other inert gas, or may be filled with a gas for calibration or a standard gas having a humidity almost the same level with the exhaled breath.

In the injection step, excess exhaled breath 203 is discharged from the outlet port 103. Although only two exhaled breath components 202*a* and 202*b* are shown in FIG. 2 (*a*) for simplification, two or more components are included in general.

In the condensation step, the electrode zone 105 is cooled by the cooling unit to no higher than the dew condensation point of the water vapor 104. As a result, condensate 204 including the water vapor, and other exhaled breath components 202*a* and 202*b* in the exhaled breath is formed on the outer peripheral surface of the electrode zone 105. FIG. 2 (*b*)

and FIG. 2 (c) illustrate the condensation step. In FIG. 2 (b), an initial stage of the condensation step is shown. FIG. 2 (b) illustrates formation of the condensate 204 on the outer peripheral surface of electrode zone 105. FIG. 2 (c) illustrates a stage of progress of the condensation step. In FIG. 2 (c), covering of the outer peripheral surface of the electrode zone 105 with the condensate 204 is shown.

In the condensation step, it is preferred that the temperature of the cooling unit 104 be controlled such that the condensate 204 is not formed in an excess amount.

In the step of forming charged fine particles, a large number of charged fine particles 205 are formed from the condensate 204. FIG. 2 (d) illustrates the step of forming charged fine particles. The form of the charged fine particles may be a cluster including one to several ten molecules, fine particles including several ten to several hundred molecules, or droplets including several hundred or more molecules. Alternatively, two or more of these forms may be present as mixtures.

The charged fine particles may also include ions or radicals derived from the exhaled breath component molecules, in addition to the electrically neutral molecules. Alternatively, these may be present as a mixture. The charged fine particles are preferably negatively charged, but may be positively charged.

The charged fine particles preferably include water and the exhaled breath components. The proportion of the water and the exhaled breath components in the charged fine particles may be the same as or different from that in the exhaled breath.

In the step of forming charged fine particles, electrostatic atomization may be preferably used for forming the charged fine particles. Principles of the electrostatic atomization are as in the following. The voltage applied between the electrode zone 105 and the counter electrode zone 106 allows the condensate 204 to be carried to the tip of the electrode zone 105. The liquid level of the condensate 204 is elevated toward the counter electrode zone 106 by coulomb attraction to give a cone shape. As the condensation further proceeds, the Coulomb force is increased due to concentration of the charge at the tip of the condensate. When the Coulomb force exceeds the surface tension of water, the condensate 204 is disrupted and scattered, whereby the charged fine particles are formed.

When the electrostatic atomization is carried out, corona discharge may be created in the case in which the relative humidity is low in the exhaled breath, the case in which the condensate is not formed enough on the outer peripheral surface of the electrode zone 105, and the like. The corona discharge may be included in the step of forming charged fine particles.

In the step of forming charged fine particles, it is preferred that the voltage applied between the electrode zone 105 and the counter electrode zone 106 be controlled depending on the electric current that flows between the electrode zone 105 and the counter electrode zone 106. When an excess electric current flows between the electrode zone 105 and the counter electrode zone 106 resulting from, for example, production the charged fine particles in excess or occurrence of the corona discharge, and the like, the voltage application between the electrode zone 105 and the counter electrode zone 106 is preferably interrupted once. The voltage applied between the electrode zone 105 and the counter electrode zone 106 may be lowered in such cases. As soon as the cause is eliminated, the voltage application may be started again.

The charged fine particle 205 has a diameter of preferably no less than 2 nm and no greater than 30 nm in light of the stability of the charged fine particles.

It is most preferred that the charge intensity applied to the charged fine particle 205 be equivalent to the elementary electric charge ($1.6 \times 10^{-19}$ C) per the fine particle. The charge intensity applied to the charged fine particle 205 is preferably greater than the elementary electric charge.

In the recovery step, the charged fine particles 205 are recovered to the chemical substance detection unit 107. FIG. 2 (e) illustrates the recovery step. It is preferred that the charged fine particles 205 are recovered by the electrostatic force in the recovery step. The voltage is applied preferably to the counter electrode zone 106 toward the chemical substance detection unit 107. When the charged fine particles 205 are negatively charged, it is preferred that positive direct current voltage be applied to the counter electrode zone 106 toward the chemical substance detection unit 107. The voltage application is preferably conducted continuously, but application in a pulsating manner is also acceptable.

In the detection step, the volatile organic compound included in the charged fine particles is detected by the chemical substance detection unit 107. It is preferred that quantitative determination of the volatile organic compound be carried out in the detection step, but only the presence of the chemical substance may be detected. In the detection step, a chemical substance detection unit calibrated beforehand is preferably used. In the present invention, the calibration method is not particularly limited.

Preferable examples of the volatile organic compound include ketones, amines, alcohols, aromatic hydrocarbons, aldehydes, esters, organic acids, hydrogen sulfide, methylmercaptan, disulfide, and the like. The volatile organic compound may be alkane, alkene, alkyne, diene, alicyclic hydrocarbon, allene, ether, carbonyl, carbanio, protein, polynuclear aromatic compounds, heterocyclic compounds, organic derivatives, biomolecules, metabolites, isoprene, isoprenoid and derivatives of the same, and the like.

The volatile organic compound has a molecular weight of preferably no lower than 15 and no higher than 500, and more preferably no lower than 30 and no higher than 400 in light of (1) ease in volatilization, and (2) high probability of inclusion in the exhaled breath.

According to World Health Organization (WHO), volatile organic compounds in a broad sense are classified into very volatile organic compounds (VVOC, boiling point: 0° C. to 50-100° C.), volatile organic compounds (VOC, boiling point: 50-100° C. to 240-260° C.), semi-volatile organic compounds (SVOC, boiling point: 240-260° C. to 380-400° C.), and particulate organic matters (POM, boiling point: no lower than 380° C.). Typical examples of VVOC include formaldehyde (molecular weight: 30, boiling point: −19.2° C.), acetaldehyde (molecular weight: 44, boiling point: 20.2° C.), and dichloromethane (molecular weight: 85, boiling point: 40° C.). Typical examples of VOC include toluene (molecular weight: 92, boiling point: 110.7° C.), xylene (molecular weight: 106, boiling point: 144° C.), benzene (molecular weight: 78, boiling point: 80.1° C.), styrene (molecular weight: 104, boiling point: 145.1° C.), and the like. Typical examples of SVOC include tributyl phosphate (molecular weight: 266, boiling point: 289° C.), dioctyl phthalate (molecular weight: 391, boiling point: 370° C.), and the like. In the present invention, the term "volatile organic compound" when merely referred to means the volatile organic compounds in such a broad sense, which include VVOC, VOC, SVOC, POM, and the like.

The volatile organic compound has a boiling point of preferably no lower than −160° C. and no higher than 400° C.

In order to reduce error sources such as the temperature variation, the humidity variation, the presence of interfering substances, the electromagnetic noise and the like, a chemical substance detection unit for correction may be provided in the vessel 101. The error sources may be reduced by differential operation of the chemical substance detection unit and the chemical substance detection unit for correction.

In the embodiment of the present invention, at least two or more steps of from the injection step to the detection step may be carried out simultaneously. More specifically, for example, the condensation step and the step of forming charged fine particles may be simultaneously carried out. Alternatively, these steps may be carried out in an orderly sequence.

In the embodiment of the present invention, it is preferred that the electrode zone 105 be heated for removing the chemical substance adhered to the electrode zone 105. When the electrode zone 105 is heated, a clean gas may be injected into the vessel 101. Other method may be employed in combination for removing the chemical substance adhered to the electrode zone 105.

In the embodiment of the present invention, for removing the chemical substance by heating the electrode zone 105, a thermoelectric element is preferably used. The thermoelectric element can be conveniently used since the cooling face and the heating face can be readily reversed. Use of single thermoelectric element for both the condensation step and removal of the chemical substance can contribute the downsizing of the analysis apparatus. The chemical substance detection unit 107 may be also used in order to detect completion of the removal of the chemical substance adhered to the electrode zone 105. For the purpose of detecting completion of the removal of the chemical substance adhered to the electrode zone 105, the outer peripheral surface of the electrode zone 105 may be provided with a detection unit, or any other known technique may be employed.

In the embodiment of the present invention, the chemical substance adhered to the electrode zone 105 is preferably removed by the airflow of a gas other than the exhaled breath. The gas is preferably a dry nitrogen gas. The gas is preferably a gas for calibration of the chemical substance detection unit.

In one aspect of the embodiment of the present invention, the exhaled breath condensate is obtained on the outer peripheral surface of the electrode zone 105 by cooling the electrode zone 105. In other words, the electrode zone has been merely a means for voltage application according to conventional analysis techniques. Therefore, it is necessary to provide a condensate reservoir vessel additionally, for retaining the exhaled breath condensate. However, a considerable time period is required for depositing the exhaled breath condensate in the condensate reservoir vessel as described above. Thus, the present invention made for solving this problem is characterized in that the electrode zone 105 has two roles. More specifically, the electrode zone 105 plays both roles of (1) an electrode for voltage application, and (2) a means for retaining the exhaled breath condensate. Accordingly, the quantity of the condensate required for the exhaled breath analysis can be significantly reduced, and the analysis time period can be shortened.

The mode for carrying out the present invention is fundamentally different from the mode of conventional minus ion mist generators in which electrostatic atomization is utilized. More specifically, according to the conventional minus ion mist generator, charged fine particles have a very small diameter of from several nm to several ten nm. Therefore, the charged fine particles float in the air for a long period of time of approximately for 10 min. In addition, the charged fine particles exhibit high diffusibility. There properties of the minus ion mist are greatly advantageous in application to moisturizing devices for skin or hair, deodorizing devices, and the like. However, these properties are advantageous in such cases as the analysis apparatus of the present invention because dilution of the chemical substance that is the detection target is rather obliged due to the floating properties and diffusibility of the charged fine particles. In order to prevent the dilution, an electrostatic atomization mechanism is provided in the closable vessel, and thus the charged fine particles including the chemical substance are efficiently recovered by the electrostatic force, according to the present invention. This event leads to another aspect of the present invention.

Embodiment 2

Figure 3:
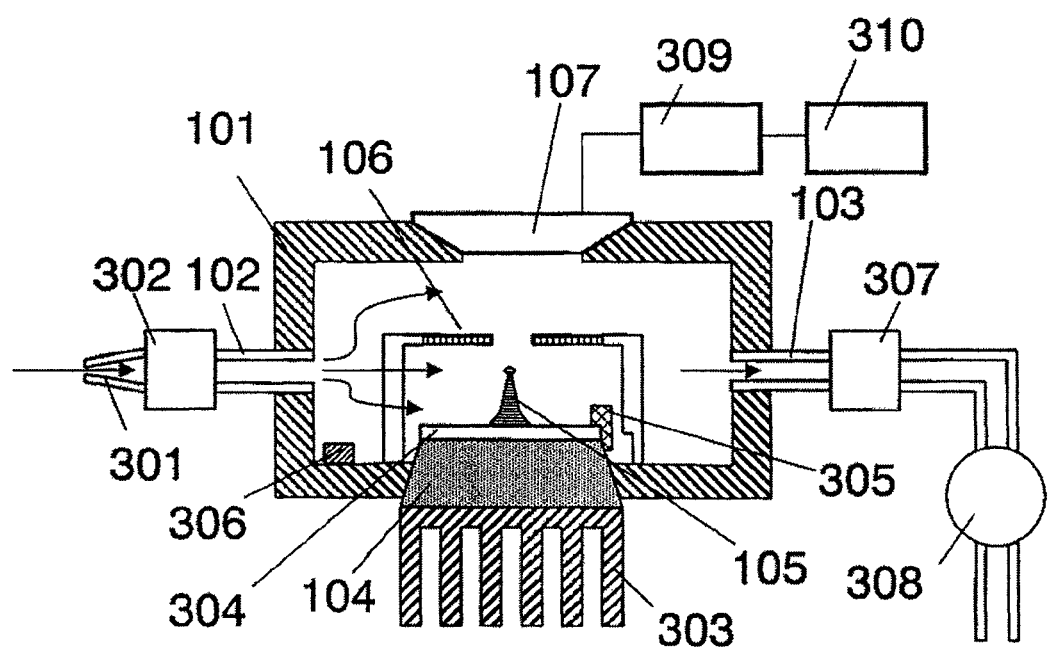
FIG. 3 shows a schematic view illustrating a breath analysis apparatus according to Embodiment 2 of the present invention.

FIG. 3 shows a schematic view illustrating a breath analysis apparatus according to Embodiment 2 of the present invention. In FIG. 3, the same constituting components as those shown in FIG. 1 are designated with the same reference signs, and their explanation is omitted.

In the embodiment of the present invention, mouthpiece 301 and trapper for saliva 302 are provided in the vicinity of the injection port 102 as shown in FIG. 3.

Since the mouthpiece 301 allows the exhaled breath to be easily injected into the vessel 101, simple operation of the breath analysis apparatus can be achieved. The mouthpiece 301 is preferably thrown away after single use from a hygienic point of view. The mouthpiece 301 is preferably formed of a silicone rubber. In the present invention, the material, the size, and the shape of the mouthpiece 301 are not particularly limited.

The trapper for saliva 302 prevents contamination of the saliva into the vessel 101 together with the exhaled breath. The trapper for saliva 302 may trap not only the saliva but also spit, sputum, food residues, dust, and the like discharged from the mouth.

In the embodiment of the present invention, the cooling unit 104 is provided with radiating zone 303 at one end thereof. The radiating zone 303 is preferably provided outside the vessel 101. It is most preferred that the radiating zone 303 be a radiating fin. The radiating zone 303 may be a cooling fan, a water jacket pipe, or other cooling means. Also, two or more of these may be used in combination.

In the embodiment of the present invention, a part of the electrode zone 105 is provided with connection portion 304. The connection portion 304 is a member that connects the cooling unit 104 with the electrode zone 105, and thermal conduction is executed via the connection portion 304. The electrode zone 105 may be also heated via the connection portion 304. In the present invention, the shape, the size, and the material of the connection portion 304 are not particularly limited.

In the embodiment of the present invention, temperature sensor 305 is provided in the vicinity of the cooling unit 104. By providing the temperature sensor 305, control of degree of the condensation is enabled. More specifically, the degree of the condensation can be freely controlled by keeping the temperature around the cooling unit 104 at a desired temperature. Also, the temperature sensor 305 may be provided in the vicinity of the electrode zone 105. The temperature sensor 305 may be also provided in the vicinity of the connection portion 304. Moreover, the temperature sensor 305 may be provided in the vicinity of the injection port 102. Further, the temperature sensor 305 may be provided inside the vessel 101. The temperature sensor 305 may be provided either alone, or in plural numbers.

In the embodiment of the present invention, it is most preferred that temperature sensor 305 be a thermocouple. The temperature sensor 305 may be a resistance temperature sensor, an infrared temperature sensor, or any other temperature sensor. The temperature sensor 305 provided may be of one type, or of several types. Also, the temperature sensor 305 may measure the temperature of the exhaled breath injected into the apparatus.

In the embodiment of the present invention, the breath analysis apparatus 100 is provided with humidity sensor 306. Since the humidity of the exhaled breath injected may vary among individuals, it is preferred that humidity sensor 306 be provided. Since the humidity sensor 306 enables the amount of saturated water vapor, dew point and the like of the exhaled breath to be determined, it is useful in inspection of preset temperatures of the cooling unit 104 and electrode zone 105, and analysis of the assay data of the components. In the present invention, the type, the number, and the position of the humidity sensor 306 are not particularly limited.

In the embodiment of the present invention, check valve 307 is provided in the vicinity of the outlet port 103. By providing the check valve 307, erroneous contamination of the ambient air and the like into the vessel 101 can be prevented in injecting the exhaled breath. The check valve 307 may be also provided in the vicinity of the injection port 102. The check valve 307 may be a diaphragm or a return check valve, or any other backflow prevention device may be also used.

In the embodiment of the present invention, pump 308 is provided in the vicinity of the check valve 307. The pump 308 assists the injection of the exhaled breath into the vessel 101. It can be suitably employed for use in the case of the subject being patients, elderly persons, infants and the like with poor expiring power of the breath, in particular. The pump 308 may be a diaphragm pump, a syringe pump, a vacuum tube, or the like. The pump 308 may be also used for injecting a gas in order to clean through the vessel 101. Further, the pump 308 may be equipped with a valve for regulating the flow rate.

In the embodiment of the present invention, the chemical substance detection unit 107 may be provided with a sensitive membrane which selectively corresponds to the chemical substance that is the detection target. In the present invention, the type, the number, the disposition, and the size of the sensitive membrane are not particularly limited. For example, the material of the sensitive membrane which may be used includes: an inorganic compound such as metal oxide, platinum, or palladium; a template polymer by molecular imprinting; an organic semiconductor material, a deoxyribonucleic acid (DNA), a ribonucleic acid (RNA), an enzyme, a biomembrane, a receptor protein, an antibody, an oligonucleotide or the like; or Langmuir-Blodgett membrane (LB membrane), or a lipid bilayer. Alternatively, multiple kinds of these materials may be used in combination.

In the embodiment of the present invention, the chemical substance detection unit 107 is provided with control unit 309 and display unit 310. The control unit 309 is a site where electrical and mechanical control of the chemical substance detection unit 107 is executed. The control unit 309 may be provided with an analysis section for analyzing the values determined in the chemical substance detection unit 107. The analysis section may execute a multi-variable analysis such as a principal component analysis, an analysis with sign and magnitude notation, a discriminative analysis, a factor analysis, a cluster analysis, a conjoint analysis or the like. Alternatively, other statistic analysis such as a multiple regression analysis may be also performed. It is preferred that the values determined with the chemical substance detection unit 107 be displayed by the display unit 310. The display unit 310 may directly display the values obtained by the control unit 309, or may display the values derived by the analysis.

In the embodiment of the present invention, the breath analysis apparatus 100 is preferably provided with an electromagnetic shielding. By providing the electromagnetic shielding, external electromagnetic noise can be shielded. Thus, detection of faint signals is permitted.

Example 1

The vessel 101 was made with a transparent acrylic resin board having a thickness of 0.5 mm. The vessel 101 was a 32 mm×17 mm×12 mm rectangular box. In order to observe the formation process of the condensate, the vessel 101 is preferably produced with a transparent body. The vessel 101 may be integrally molded.

The injection port 102 was formed after a through-hole having a diameter of 3 mm was formed at one end of the vessel 101, by connecting to a silicone tube having an external diameter of 3 mm. In the present invention, the method of forming the injection port 102 is not particularly limited. The injection port 102 may be formed concomitant with integral molding of the vessel 101, or cutting processing may be adopted for the formation. Alternatively, the injection port 102 may be formed by any other general method such as dry etching, hot embossing, nanoimprint or the like.

The outlet port 103 was formed after a through-hole having a diameter of 3 mm formed at the other end of the vessel 101, by connecting a silicone tube having an external diameter of 3 mm. In the present invention, the method of forming the outlet port 103 is not particularly limited. The outlet port 103 may be formed concomitantly with the integral molding of the vessel 101, or may be formed by cutting processing. Alternatively, outlet port 103 may be formed by any other general method such as dry etching, hot embossing, nanoimprint or the like.

A thermoelectric element was provided inside the vessel 101, as the cooling unit 104. The thermoelectric element had a size of 14 mm×14 mm×1 mm. The endothermal maximum of the thermoelectric element was 0.9 W. The maximum temperature difference of the thermoelectric element was 69° C. The thermoelectric element was provided with a radiating fin. The cooling face of the thermoelectric element was covered with a ceramic material. Since the ceramic material has a fine uneven or porous structure on the surface thereof, the material body being in contact can be efficiently cooled. In this Example, the thermoelectric element was provided at one site, but multiple thermoelectric elements may be provided at multiple sites.

As the electrode zone 105, a stainless steel pin was provided inside the vessel 101 and in the vicinity of the cooling unit 104. The electrode zone 105 had a length of 3 mm. The electrode zone 105 had a diameter of 0.79 mm at the largest part, and of 0.5 mm at the smallest part. A sphere having a diameter of 0.72 mm was provided at the tip of the electrode zone 105, whereby the step of forming charged fine particles could be carried out in a stable manner. The electrode zone 105 was to be in contact with the thermoelectric element of the cooling unit 104 via a stainless steel plate. The size of the stainless steel plate had a size of 10 mm×10 mm×1 mm. The stainless steel plate was to be in contact with the thermoelectric element by means of a well-thermally conductive resin.

The counter electrode zone 106 was provided at a place 3 mm away from the tip of the electrode zone 105. The counter electrode zone 106 had a circular shape with an external diameter of 12 mm, an internal diameter of 8 mm, and a thickness of 0.47 mm. The material of the counter electrode zone 106 was stainless steel.

The chemical substance detection unit 107 was constituted with an electrode which can be cooled, a syringe, and a gas chromatograph. A part of the chemical substance detection unit 107 was cooled by a thermoelectric element. The thermoelectric element had a size of 14 mm×14 mm×1 mm. The endothermal maximum of the thermoelectric element was 0.9 W. The maximum temperature difference of the thermoelectric element was 69° C. The thermoelectric element was provided with a radiating fin. The gas chromatograph employed was GC-4000 manufactured by GL Sciences Inc.

The injection port 102 and the outlet port 103 were provided with valve 108a and valve 108b, respectively. A ball valve was used as the valve 108a and valve 108b.

Next, procedures for operating the breath analysis apparatus are explained.

In the injection step, the exhaled breath model gas was injected from the injection port 102 into the vessel 101. In this Example, the vessel 101 had a volume of 6.5 mL, which was small enough as compared with adult pulmonary capacity (approximately 2,000 to 4,000 cc). Thus, when the exhaled breath model gas was blown for several seconds, it can be regarded that the vessel 101 could be filled with the exhaled breath model gas.

The exhaled breath model gas was obtained by introducing a dry nitrogen gas into water and a 0.3% aqueous acetic acid solution, followed by bubbling. The flow rate of the dry nitrogen gas was 500 sccm. The exhaled breath model gas had a temperature of 25° C. This exhaled breath model gas was used on the grounds that: (a) acetic acid components are included in real exhaled breath components (Nonpatent Document 4, page 297); (b) a volatile organic compound was included; and (c) it is more readily available than the real exhaled breath for quantitatively evaluating the effects of the breath analysis apparatus of the present invention with favorable reproducibility.

In the injection step, before injecting the exhaled breath model gas into the vessel 101, the vessel 101 was filled with a dry nitrogen gas.

In the injection step, excess exhaled breath model gas was discharged through the outlet port 103.

In the condensation step, the electrode zone 105 was cooled by the thermoelectric element. The temperature of the electrode zone 105 was 26° C. before the operation, and lowered to 15° C. 30 seconds later. The temperature of the electrode zone 105 was measured with a K type thermocouple.

Figure 4:
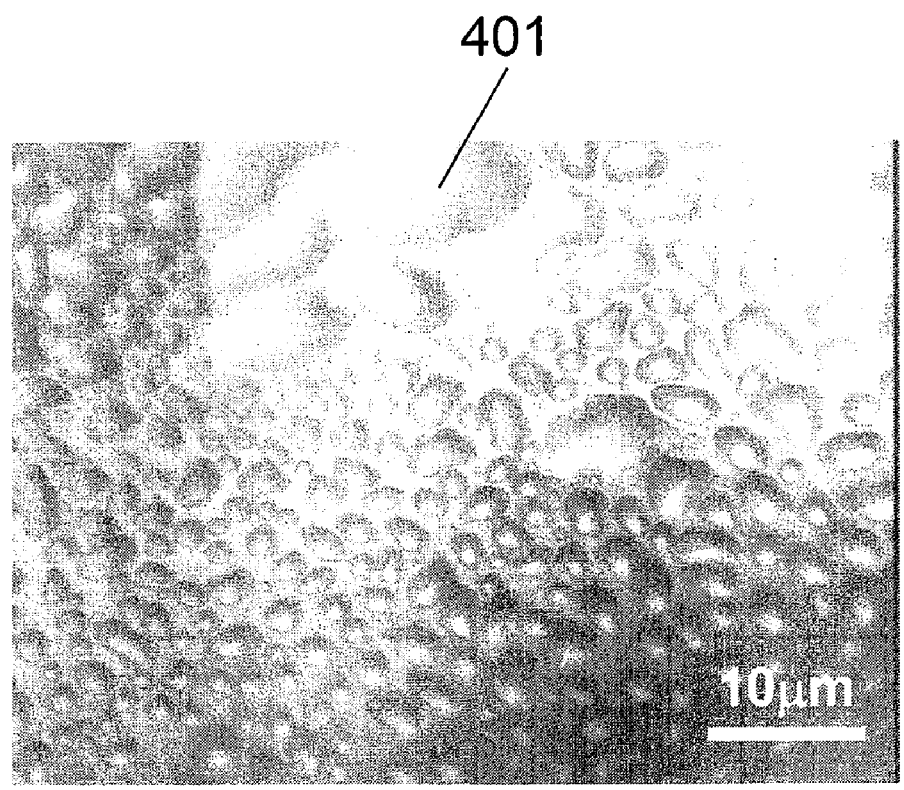
FIG. 4 shows a micrograph of the electrode zone surface in the condensation step.

After 5 seconds following starting operation of the thermoelectric element, the condensate was formed on the outer peripheral surface of the electrode zone 105. In the initial stage, the condensate was droplets having a diameter of no greater than 10 μm. The droplet condensate was grown over time, and thus a sufficient amount of the liquid for analysis was obtained. The formation of the condensate on the electrode zone 105 was observed using a microscope (VH-6300, manufactured by KEYENCE Corporation). FIG. 4 shows the state of formation of the exhaled breath condensate on the outer peripheral surface of the electrode zone 105. As shown in FIG. 4, the condensate 401 was formed on the outer peripheral surface of the electrode zone 105.

In the step of forming charged fine particles, the condensate was turned into a large number of charged fine particles. The formation of the charged fine particles was carried out by electrostatic atomization. The formation of the charged fine particles of the present invention may be also carried out by corona discharge.

The diameter of the charged fine particles is preferably no less than 2 nm and no greater than 30 nm in light of the stability of the charged fine particles. It is preferred that each one of the charged fine particles exists independently. The charged fine particles may be present as aggregates of multiple particles. In the present invention, the form of the exhaled breath turned into fine particles is not particularly limited, which may be spherical, brad oblate, or spindle.

DC of 5 kV was applied between the electrode zone 105 and the counter electrode zone 106. In this procedure, a cathode was employed as the electrode zone 105, whole an anode was employed as the counter electrode zone 106. Although similar effects can be achieved by inverse setting, i.e., an anode as the electrode zone 105, and a cathode as the counter electrode 106, the step of forming charged fine particles was comparatively unstabilized.

Figure 5:
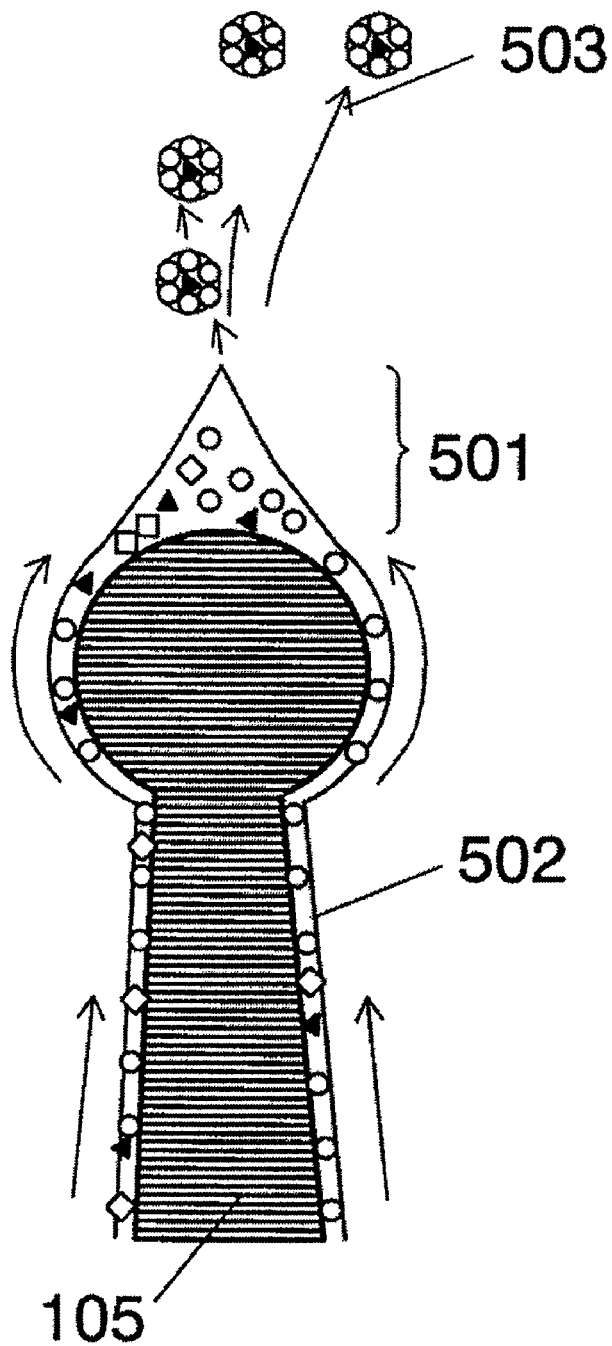
FIG. 5 shows an explanatory view illustrating the step of forming charged fine particles.
Figure 6:
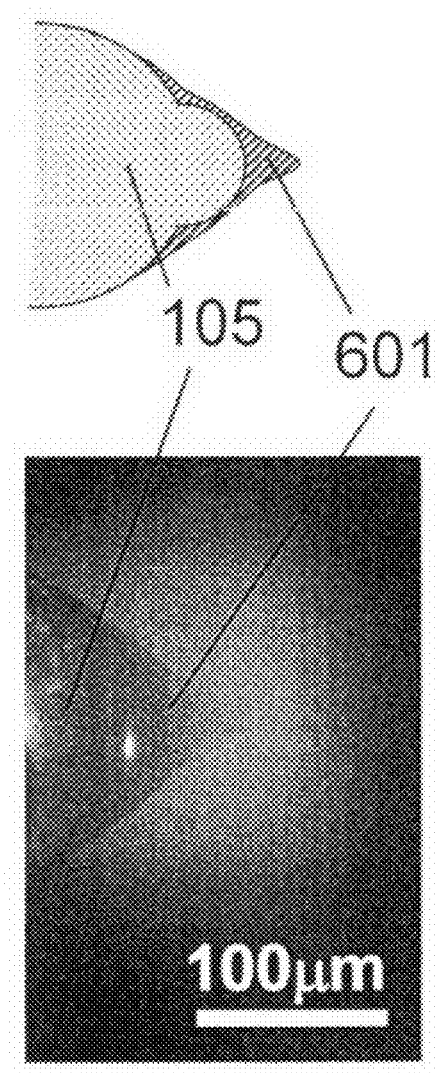
FIG. 6 shows an explanatory view and a micrograph illustrating the tip portion of the electrode zone in the step of forming charged fine particles.

In the step of forming charged fine particles, a water column having a cone shape, referred to as Taylor cone, was formed at the tip of the electrode zone 105. From the tip of the water column, a large number of the charged fine particles including the chemical substance were released. FIG. 5 illustrates production of the Taylor cone and the charged fine particles. The condensate 502 that forms Taylor cone 501 was transferred serially in the direction toward the tip of the electrode zone 105. The charged fine particles 503 were formed from the leading edge of the Taylor cone 501, i.e., the place where the electric voltage is concentrated FIG. 6 illustrates a Taylor cone formed with the exhaled breath condensate. Taylor cone 601 was formed after 7 seconds following starting the injection of the exhaled breath model gas.

In the step of forming charged fine particles, the electric current that flows between the electrode zone 105 and the counter electrode zone 106 was measured. When an excess electric current flow was found, the voltage application between the electrode zone 105 and the counter electrode zone 106 was interrupted, or the applied voltage was reduced.

In the recovery step, the charged fine particles were recovered into the chemical substance detection unit 107 by means of the electrostatic force. A voltage of +500 V was applied to the counter electrode 106 toward the chemical substance detection unit 107. In the present invention, the intensity of the applied voltage is not limited. In light of the life span of the charged fine particles, the recovery step is most preferably carried out concomitantly with the step of forming charged fine particles, and the recovery step is preferably carried out no later than 10 minutes after starting the step of forming the charged fine particles.

The charged fine particles recovered with the electrostatic force were reliquidified by cold condensation. The charged fine particles thus recovered are most preferably liquidified, but keeping the mist form is also acceptable. When liquidification is carried out, the charged fine particles may be subjected to cold condensation, or may be dissolved in an aqueous solution or gel.

Figure 7:
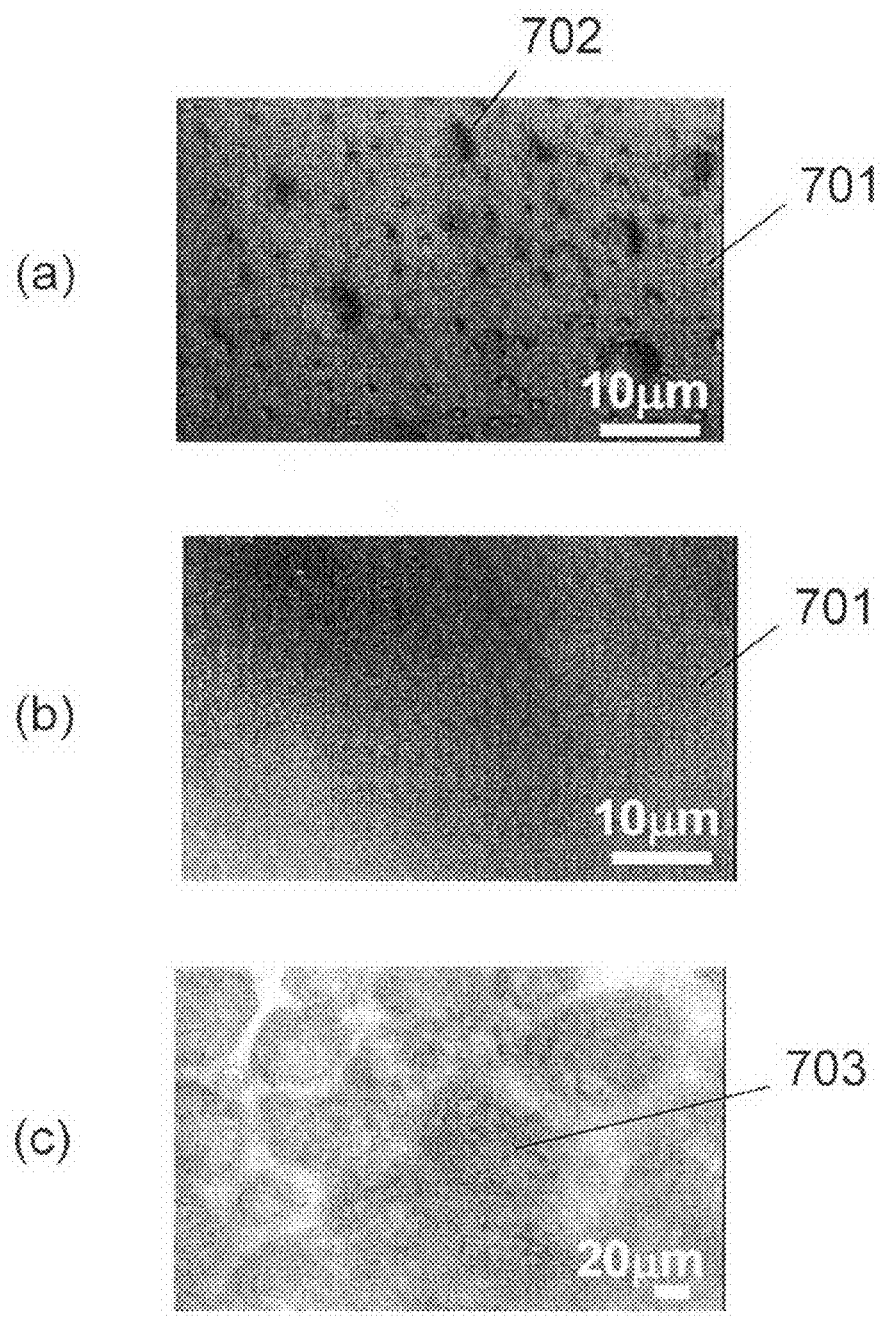
FIG. 7 shows a micrograph illustrating the second electrode zone in the recovery step according to the present invention.

Although the chemical substance detection unit 107 was constituted with an electrode which can be cooled, a syringe, and a gas chromatograph, FIG. 7 illustrates the state of cold condensation of the charged fine particles again on the electrode which can be cooled, i.e., the outer peripheral surface of the second electrode zone 701. The state of the cold condensation was observed using a microscope (VH-6300, manufactured by KEYENCE Corporation).

FIG. 7 (a) illustrates the state of the cold condensation when the second electrode zone 701 was allowed to have a temperature of 12° C. The condensate 702 was formed on the outer peripheral surface of the second electrode zone 701. FIG. 7 (b) illustrates the state of the cold condensation when the second electrode zone 701 was allowed to have a temperature of 22° C. The condensate 702 was not formed on the outer peripheral surface of the second electrode zone 701. FIG. 7 (c) illustrates the state of the cold condensation when the second electrode zone 701 was allowed to have a temperature of −5° C. Aggregate 703 was formed on the outer peripheral surface of the second electrode zone 701 by coaggregation of the condensate 702.

TABLE 1

| Second electrode temperature | Volume of condensate (μL) |
| --- | --- |
| −5 | 0 |
| 7 | 1.4 |
| 12 | 0.7 |
| 18 | 0.5 |
| 22 | 0 |
| 30 | 0 |

Table 1 shows relationship between the temperature of the second electrode zone 701, and the volume of the liquid of the condensate 702. The volume of the liquid of the condensate 702 was defined as a volume obtained in the recovery step carried out for 6 min. When the temperature of the second electrode was lowered to −5° C., the condensate 702 started to coaggregate, therefore, the volume of the liquid was defined as 0. When the temperature of the second electrode zone 701 was no higher than 0° C., the condensate 702 was coaggregated. Accordingly, the temperature of the second electrode zone 701 is preferably no lower than 0° C. and no higher than 18° C. Since the condensate 702 can be obtained in a short period of time, the temperature of the second electrode zone 701 is more preferably no lower than 0° C. and no higher than 7° C. In addition, the coaggregated condensate 702 may be reliquidified by heating.

In the recovery step, the cold condensation of the charged fine particles was executed by lowering the temperature of the second electrode zone 701 to 12° C. Thus resulting condensate of 1 μL was collected with a syringe, and introduced into the gas chromatograph.

Figure 8:
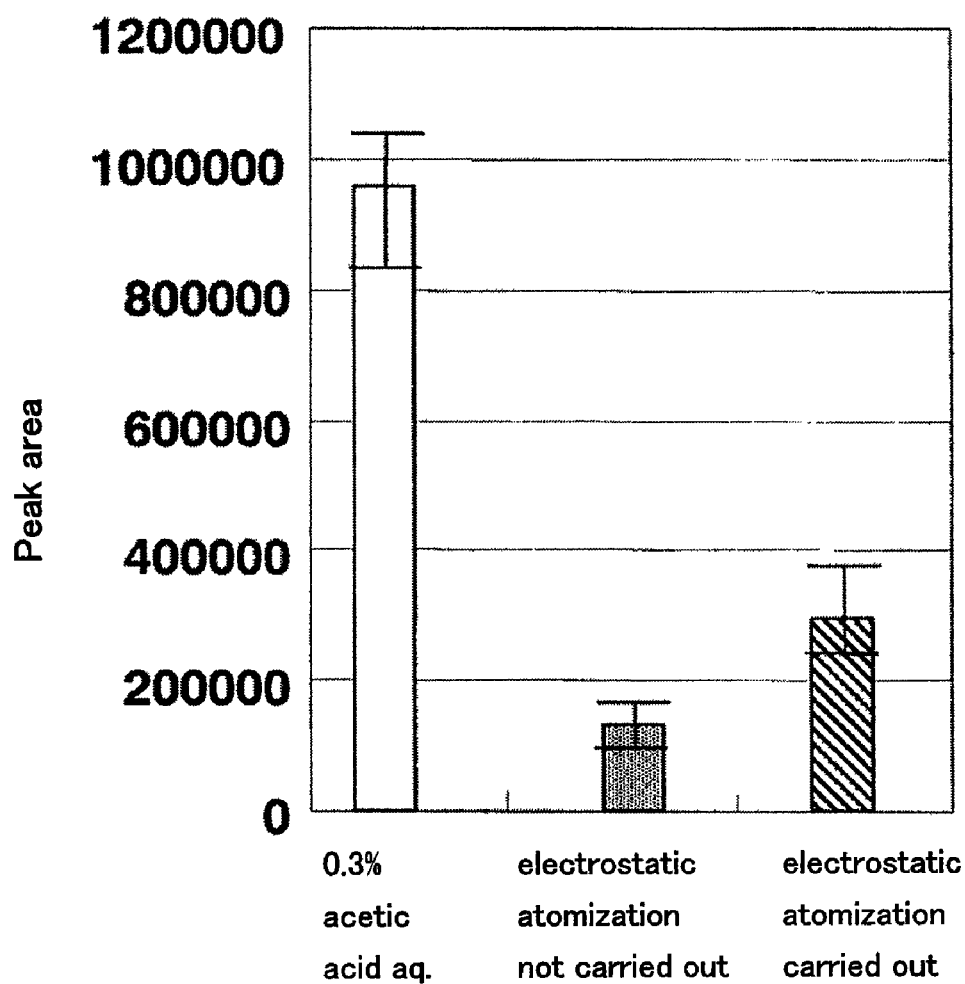
FIG. 8 shows a view illustrating an exemplary analysis of exhaled breath in the detection step according to the present invention.

In the detection step, the exhaled breath condensate introduced into the gas chromatograph was analyzed. FIG. 8 shows an example of analysis of an exhaled breath component, i.e., acetic acid. The vertical axis indicates the peak area of the gas chromatogram of acetic acid. The greater peak area means the higher concentration of acetic acid. As a reference, the results of a 0.3% aqueous acetic acid solution was shown (bar graph on the left side in FIG. 8). For comparison, the results achieved by an example in which the cold condensation of the exhaled breath was merely carried out without employing the electrostatic atomization (bar graph on the middle side in FIG. 8). When the exhaled breath was analyzed employing the electrostatic atomization (bar graph on the right side in FIG. 8), the concentration effect about twice was achieved as compared with the case in which electrostatic atomization was not employed. This result suggests that a time period required for collecting the same quantity of the exhaled breath components can be reduced to about half as compared with the case in which a conventional apparatus was used. Thus, it is revealed that the exhaled breath can be efficiently analyzed according to the present invention.

It should be noted that the detection conditions were as follows. As the analytical column, a capillary column (TC-FFAP, manufactured by GL Sciences Inc.) was used. The capillary column had an internal diameter of 0.53 mm, and a length of 30 m. The carrier gas was a helium gas. The oven temperature was 160° C. The injection temperature and the flame ionization detector (FID) temperature were 250° C., respectively.

Following the detection step, the chemical substance detection unit 107 was detached from the vessel 101. The detached chemical substance detection unit 107 was washed with methanol.

Following the detection step, in order to remove the chemical substance adhered to the electrode zone 105, the electrode zone 105 was heated. The electrode zone 105 was heated with a thermoelectric element. The thermoelectric element employed was the same as that used in cooling the electrode zone 105 in the condensation step. When the electrode zone 105 was heated, the polarity of the voltage applied to the thermoelectric element was reversed from the polarity in cooling the electrode zone 105.

In order to remove the chemical substance adhered by heating the electrode zone 105, the electrode zone 105 was exposed to an airflow of a dry nitrogen gas. Thus, removal of the chemical substance from the electrode zone 105 could be rapidly carried out. The dry nitrogen gas was introduced from the injection port 102.

In the step of forming charged fine particles or the recovery step, the static elimination of the chemical substance detection unit 107 was carried out. The static elimination was carried out by ground of the chemical substance detection unit 107.

In the step of forming charged fine particles, the electric current that flows between the counter electrode zone 106 and the electrode zone 105 was monitored. When an excess electric current flow was found, the voltage application between the electrode zone 105 and the counter electrode zone 106 was interrupted.

Figure 9:
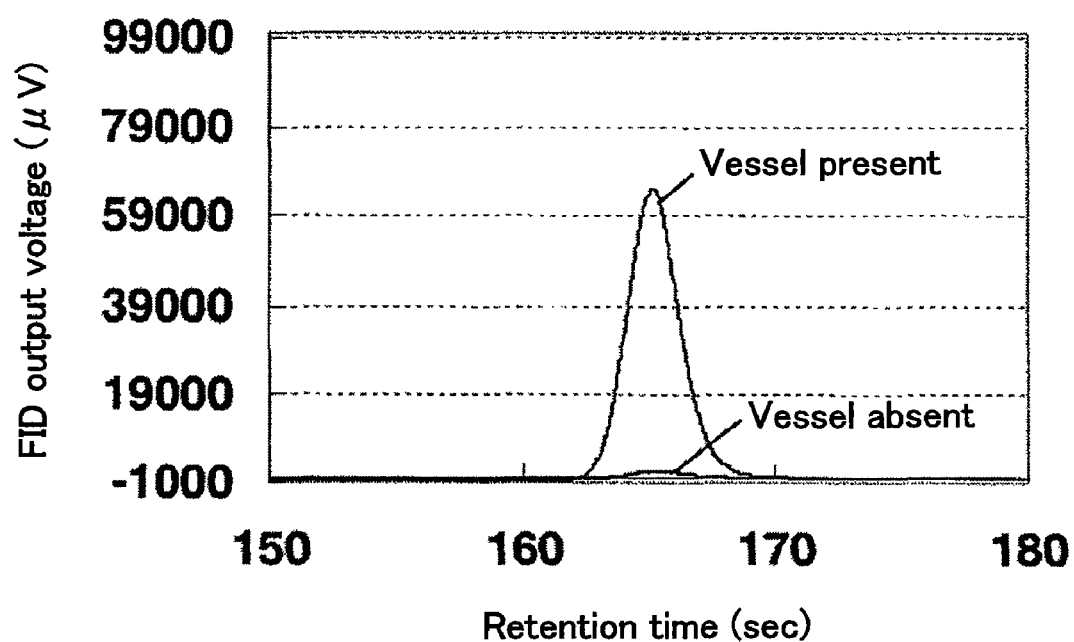
FIG. 9 shows a view illustrating an exemplary analysis of exhaled breath in the detection step according to the present invention.

FIG. 9 illustrates results of the exhaled breath analyses in the cases in which the vessel 101 was or was not provided. When the closable vessel 101 was provided, the exhaled breath could be analyzed more efficiently than the case in which the vessel 101 was not provided. When a conventional apparatus was used, 10 min or longer was required for obtaining the condensate. However, in this Example, substantial amount of time required from start of the injection of the exhaled breath, including the detection step was about 3 min. As a result, the time period required for the analysis could be shortened.

When the conventional cooling condensation apparatus was used, a long period of time is required since the operation of dealing with a condensate collecting vessel is accompanied. However, according to the present invention, the exhaled breath components can be more efficiently concentrated as compared with the case in which the exhaled breath analysis was carried out with conventional cold condensation alone, and thus the analysis time period could be shortened Example 2

In this Example, human exhaled breath was analyzed. In this Example, since the same breath analysis apparatus as that in Example 1 was used, explanation of the breath analysis apparatus is omitted.

Procedures for operating the breath analysis apparatus are explained next.

In the injection step, the exhaled breath was injected from the injection port 102 into the vessel 101. First, 500 mL of the exhaled breath was collected into a sampler bag (volume: 1 L, aluminum coating). Thereafter, the exhaled breath was injected from the sampler bag into the vessel 101 through the injection port 102.

In the injection step, before injecting the exhaled breath into the vessel 101, the vessel 101 was filled with a dry nitrogen gas.

In the injection step, excess exhaled breath was discharged through the outlet port 103.

In the condensation step, the electrode zone 105 was cooled by the thermoelectric element. The temperature of the electrode zone 105 was 26° C. before the operation, and lowered to 15° C. 30 seconds later. The measurement of the temperature of the electrode zone 105 was carried out with a K type thermocouple.

After 5 seconds following starting operation of the thermoelectric element, the condensate started to be formed on the outer peripheral surface of the electrode zone 105. In the initial stage, the condensate was droplets having a diameter of no greater than 10 μm. The droplet condensate was grown over time, and thus a sufficient amount of the liquid for analysis was obtained.

In the step of forming charged fine particles, the condensate was turned into a large number of charged fine particles. The formation of the charged fine particles was carried out with electrostatic atomization. As is also described in the above Embodiment 1, the corona discharge is created at the initial stage of the electrostatic atomization, the step of forming charged fine particles of the present invention may also include may involve the same.

The diameter of the charged fine particles is preferably no less than 2 nm and no greater than 30 nm in light of the stability of the charged fine particles. It is preferred that each one of the charged fine particles exists independently. A plurality of the charged fine particles may be present as aggregates. In the present invention, the form of the exhaled breath turned into fine particles is not particularly limited, which may be spherical, brad oblate, or spindle.

DC of 5 kV was applied between the electrode zone 105 and the counter electrode zone 106. In this procedure, a cathode was employed as the electrode zone 105, whole an anode was employed as the counter electrode zone 106. Although similar effects can be achieved by inverse setting, i.e., an anode as the electrode zone 105, and a cathode as the counter electrode 106, the step of forming charged fine particles was comparatively unstabilized.

In the step of forming charged fine particles, a water column having a cone shape, referred to as Taylor cone, was formed at the tip of the electrode zone 105. From the tip of the water column, a large number of the charged fine particles including the chemical substance were released.

Taylor cone 601 was formed after 7 seconds following starting the injection of the exhaled breath.

In the step of forming charged fine particles, the electric current that flows between the electrode zone 105 and the counter electrode zone 106 was measured. When an excess electric current flow was found, the voltage application between the electrode zone 105 and the counter electrode zone 106 was interrupted, or the applied voltage was reduced.

In the recovery step, the charged fine particles were recovered into the chemical substance detection unit 107 by means of the electrostatic force. A voltage of +500 V was applied to the counter electrode 106 toward the chemical substance detection unit 107. In the present invention, the intensity of the applied voltage is not limited. In light of the life span of the charged fine particles, the recovery step is most preferably carried out concomitantly with the step of forming charged fine particles, and the recovery step is preferably carried out no later than 10 minutes after starting the step of forming the charged fine particles.

The charged fine particles recovered with the electrostatic force were reliquidified by cold condensation. The charged fine particles thus recovered are most preferably liquidified, but keeping the mist form is also acceptable. When liquidification is carried out, the charged fine particles may be subjected to cold condensation, or may be dissolved in an aqueous solution or gel.

In the recovery step, the cold condensation of the charged fine particles was executed by lowering the temperature of the second electrode zone 701 to 12° C. Thus resulting condensate 702 of 1 μL was collected with a syringe, and introduced into the gas chromatograph.

Figure 10:
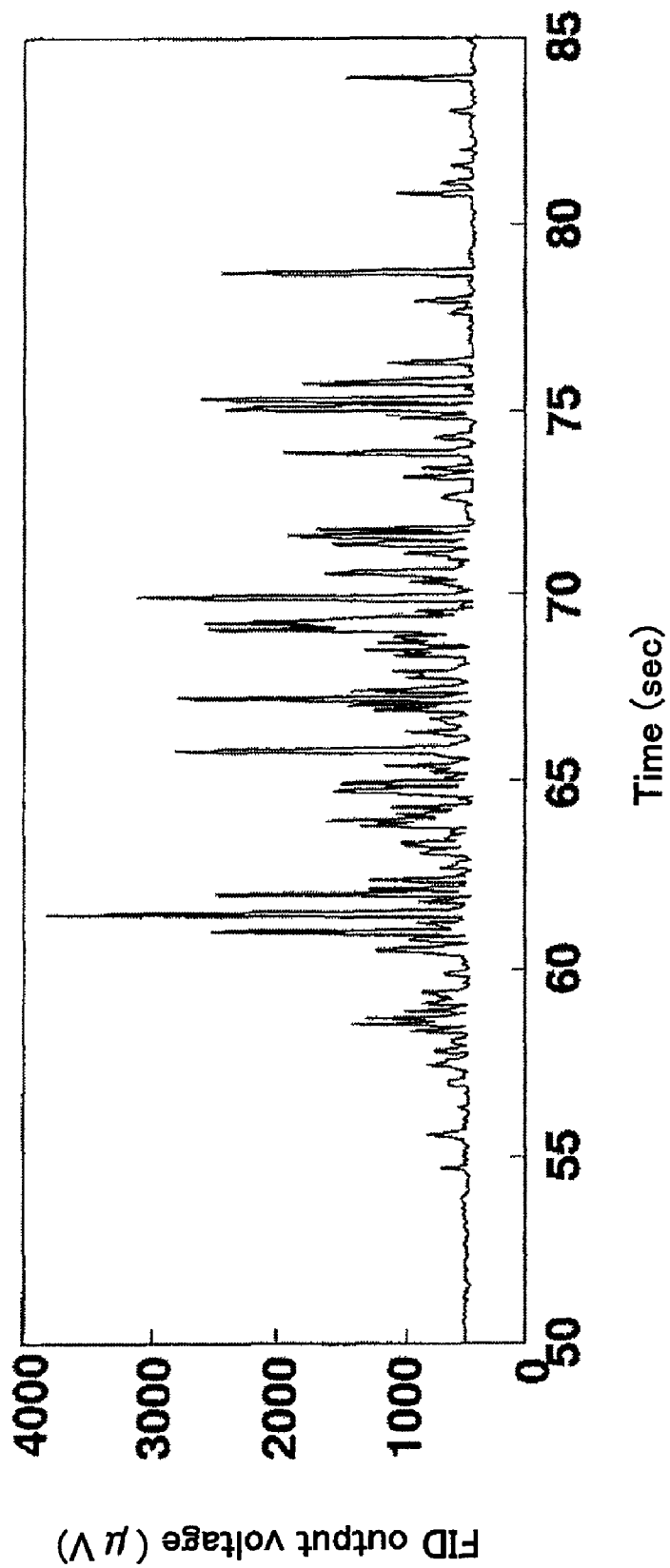
FIG. 10 shows a view illustrating an exemplary analysis of exhaled breath in the detection step according to the present invention.
Figure 11:
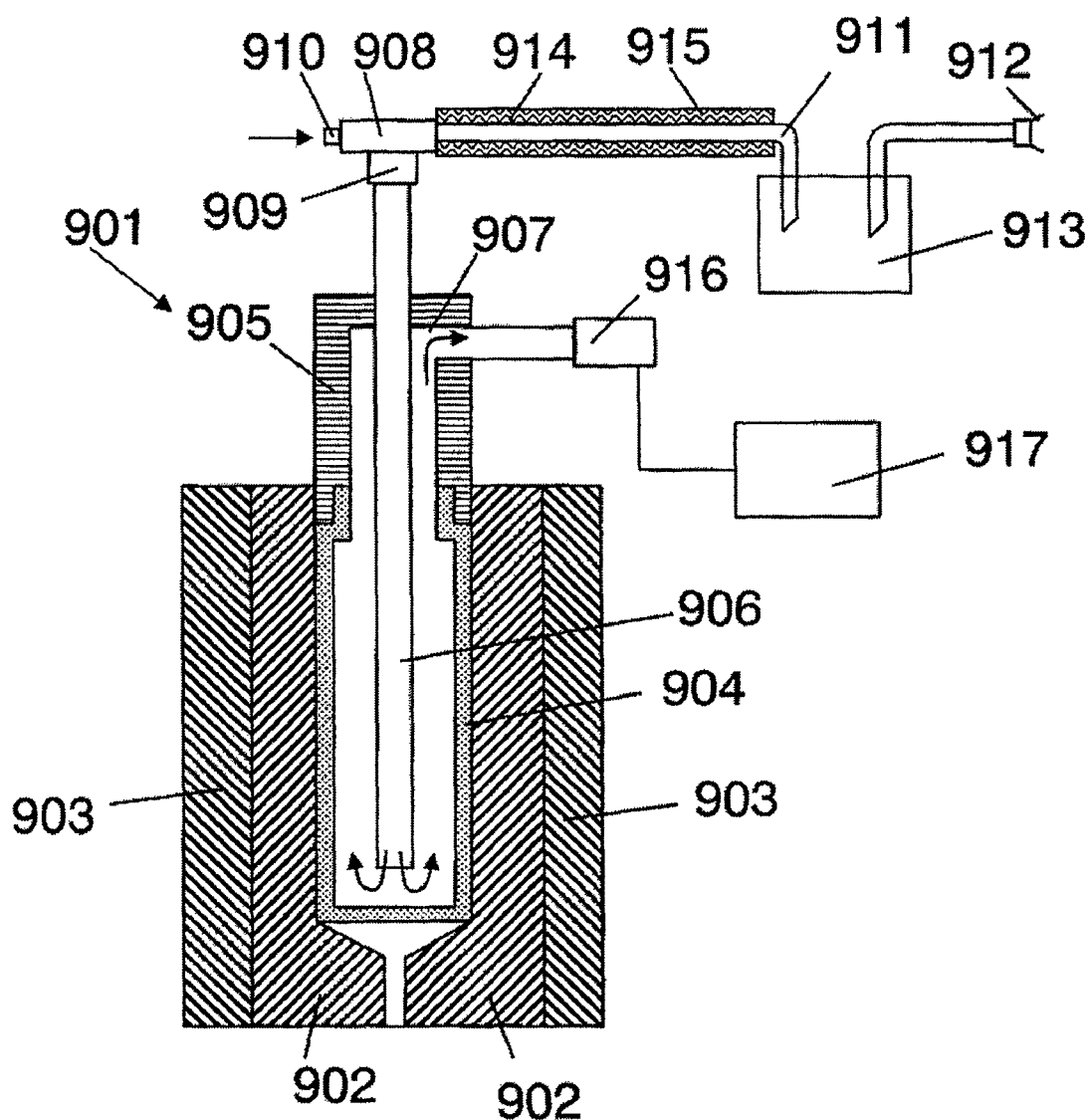
FIG. 11 shows a schematic view illustrating a conventional breath analysis apparatus.
Figure 12:
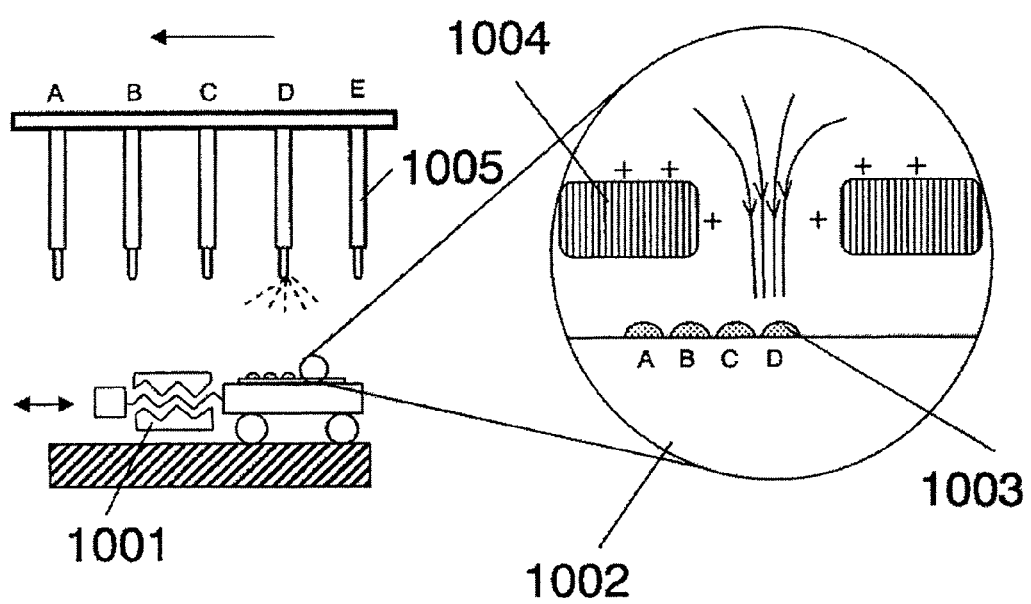
FIG. 12 shows a schematic view illustrating a conventional breath analysis apparatus.

In the detection step, the exhaled breath condensate introduced into the gas chromatograph was analyzed. FIG. 10 shows an example of analysis of the exhaled breath. The volatile organic compound included in the exhaled breath was detected.

It should be noted that the detection conditions were as follows. As the analytical column, a capillary column (TC-FFAP, manufactured by GL Sciences Inc.) was used. The capillary column had an internal diameter of 0.53 mm, and a length of 30 m. The carrier gas was a helium gas. The oven temperature was 160° C. The injection temperature and the flame ionization detector (FID) temperature were 250° C., respectively.

Substantial amount of time required from start of the injection of the exhaled breath, including the detection step was about 3 min. According to the present invention, human exhaled breath could be analyzed conveniently in a short period of time.

Example 3

The vessel 101 was made with an aluminum plate having a thickness of 4 mm. The vessel 101 was a 34 mm×34 mm×20 mm rectangular box.

The injection port 102 was formed by connecting a stainless steel tube having an external diameter of 3.17 mm and a length of 50 mm at one end of the vessel 101.

The outlet port 103 was formed by connecting a stainless steel tube having an external diameter of 3.17 mm and a length of 50 mm at the other end of the vessel 101.

A thermoelectric element was provided as the cooling unit 104, inside the vessel 101. The thermoelectric element had a size of 14 mm×14 mm×1 mm. The endothermal maximum of the thermoelectric element was 0.9 W. The maximum temperature difference of the thermoelectric element was 69° C. The thermoelectric element was provided with a radiating fin. The cooling face of the thermoelectric element was covered with a ceramic material. Since the ceramic material has a fine uneven or porous structure on the surface thereof, the material body being in contact can be efficiently cooled. In this Example, the thermoelectric element was provided at one site, but multiple thermoelectric elements may be provided at multiple sites.

As the electrode zone 105, a stainless steel pin was provided inside the vessel 101 and in the vicinity of the cooling unit 104. The electrode zone 105 had a length of 3 mm. The electrode zone 105 had a diameter of 0.79 mm at the largest part, and of 0.5 mm at the smallest part. A sphere having a diameter of 0.72 mm was provided at the tip of the electrode zone 105, whereby the step of forming charged fine particles could be carried out in a stable manner. The electrode zone 105 was to be in contact with the thermoelectric element of the cooling unit 104 via a stainless steel plate. The size of the stainless steel plate had a size of 10 mm×10 mm×1 mm. The stainless steel plate was to be in contact with the thermoelectric element by means of a well-thermally conductive resin.

The counter electrode zone 106 was provided at a place 3 mm away from the tip of the electrode zone 105. The counter electrode zone 106 had a circular shape with an external diameter of 12 mm, an internal diameter of 8 mm, and a thickness of 0.47 mm. The material of the counter electrode zone 106 was stainless steel.

The chemical substance detection unit 107 was constituted with an electrode which can be cooled, a syringe, and a gas chromatograph. A part of the chemical substance detection unit 107 was cooled by a thermoelectric element. The thermoelectric element had a size of 14 mm×14 mm×1 mm. The endothermal maximum of the thermoelectric element was 0.9 W. The maximum temperature difference of the thermoelectric element was 69° C. The thermoelectric element was provided with a radiating fin. The gas chromatograph employed was GC-4000 manufactured by GL Sciences Inc.

The injection port 102 and the outlet port 103 were provided with valve 108a and valve 108b, respectively. A ball valve was used as the valve 108a and valve 108b.

Next, procedures for operating the breath analysis apparatus are explained.

In the injection step, the exhaled breath model gas was injected from the injection port 102 into the vessel 101. In this Example, the vessel 101 had a volume of 6.5 mL, which was small enough as compared with adult pulmonary capacity (approximately 2,000 to 4,000 cc). Thus, when the exhaled breath model gas was blown for several seconds, it can be regarded that the vessel 101 could be filled with the exhaled breath model gas.

The exhaled breath model gas was obtained by introducing a dry nitrogen gas into water and an organic solution (acetic acid (molecular weight: 60.05), 2-propanol (molecular weight: 60.10), xylene (molecular weight: 106.17), methyl salicylate (molecular weight: 152.15), and menthol (molecular weight: 156.27)), followed by bubbling. The flow rate of the dry nitrogen gas was 500 sccm. Any of the components in the aforementioned organic solution is a volatile organic compound.

In the injection step, before injecting the exhaled breath model gas into the vessel 101, the vessel 101 was filled with a dry nitrogen gas.

In the injection step, excess exhaled breath model gas was discharged through the outlet port 103.

In the condensation step, the electrode zone 105 was cooled by the thermoelectric element. The temperature of the electrode zone 105 was 26° C. before the operation, and lowered to 15° C. 30 seconds later. The temperature of the electrode zone 105 was measured with a K type thermocouple.

After 5 seconds following starting operation of the thermoelectric element, the condensate was formed on the outer peripheral surface of the electrode zone 105. In the initial stage, the condensate was droplets having a diameter of no greater than 10 μm. The droplet condensate was grown over time, and thus a sufficient amount of the liquid for analysis was obtained.

In the step of forming charged fine particles, the condensate was turned into a large number of charged fine particles. The formation of the charged fine particles was carried out by electrostatic atomization. The formation of the charged fine particles of the present invention may be also carried out by corona discharge.

The diameter of the charged fine particles is preferably no less than 2 nm and no greater than 30 nm in light of the stability of the charged fine particles. It is preferred that each one of the charged fine particles exists independently. The charged fine particles may be present as aggregates of multiple particles. In the present invention, the form of the exhaled breath turned into fine particles is not particularly limited, which may be spherical, brad oblate, or spindle.

DC of 5 kV was applied between the electrode zone 105 and the counter electrode zone 106. In this procedure, a cathode was employed as the electrode zone 105, whole an anode was employed as the counter electrode zone 106. Although similar effects can be achieved by inverse setting, i.e., an anode as the electrode zone 105, and a cathode as the counter electrode 106, the step of forming charged fine particles was comparatively unstabilized.

In the step of forming charged fine particles, a water column having a cone shape, referred to as Taylor cone, was formed at the tip of the electrode zone 105. From the tip of the water column, a large number of the charged fine particles including the chemical substance were released.

Taylor cone 601 was formed after 7 seconds following starting the injection of the exhaled breath model gas.

In the step of forming charged fine particles, the electric current that flows between the electrode zone 105 and the counter electrode zone 106 was measured. When an excess electric current flow was found, the voltage application between the electrode zone 105 and the counter electrode zone 106 was interrupted, or the applied voltage was reduced.

In the recovery step, the charged fine particles were recovered into the chemical substance detection unit 107 by means of the electrostatic force. A voltage of +500 V was applied to the counter electrode 106 toward the chemical substance detection unit 107. In the present invention, the intensity of the applied voltage is not limited. In light of the life span of the charged fine particles, the recovery step is most preferably carried out concomitantly with the step of forming charged fine particles, and the recovery step is preferably carried out no later than 10 minutes after starting the step of forming the charged fine particles.

The charged fine particles recovered with the electrostatic force were reliquidified by cold condensation. The charged fine particles thus recovered are most preferably liquidified, but keeping the mist form is also acceptable. When liquidification is carried out, the charged fine particles may be subjected to cold condensation, or may be dissolved in an aqueous solution or gel.

In the recovery step, the cold condensation of the charged fine particles was executed by lowering the temperature of the second electrode zone 701 to 12° C. Thus resulting condensate 702 of 1 μL was collected with a syringe, and introduced into the gas chromatograph.

TABLE 2

|  | Molecular weight | Concentration ratio |
| --- | --- | --- |
| Acetic acid | 60.05 | 44000 |
| 2-propanol | 60.10 | 1000 |
| Xylene | 106.17 | 1600 |
| Methyl salicylate | 152.15 | 41000 |
| Menthol | 156.27 | 66000 |
| Sclareol | 308.50 | 2900 |

Table 2 shows examples of the analysis of volatile organic compounds, i.e., acetic acid, 2-propanol, xylene, methyl salicylate, menthol and sclareol. In Table 2, the concentration ratio means a ratio of the concentration of the volatile component included in the condensate 702 to the concentration of the volatile component included in the exhaled breath model gas per unit volume.

As shown in Table 2, the effect on concentration was exhibited for any of the volatile organic compounds, suggesting that the exhaled breath can be analyzed efficiently. The volatile organic compound has a molecular weight of preferably no lower than 12 and no higher than 500, and more preferably no lower than 30 and no higher than 300.

It should be noted that the detection conditions were as follows. As the analytical column, a capillary column (INERTCAP PURE WAX, manufactured by GL Sciences Inc.) was used. The capillary column had an internal diameter of 0.25 mm, and a length of 30 m. The carrier gas was a helium gas. The oven temperature was 160° C. The injection temperature and the flame ionization detector (FID) temperature were 250° C., respectively.

In this Example, it was suggested that the volatile organic compounds can be readily concentrated. As is seen from these results, the exhaled breath can be analyzed conveniently in a short period of time according to the present invention.

From the foregoing description, many modifications and other embodiments of the present invention are apparent to persons skilled in the art. Accordingly, the foregoing description should be construed merely as an illustrative example, which was provided for the purpose of teaching best modes for carrying out the present invention to persons skilled in the art. Details of the construction and/or function of the present invention can be substantially altered without departing from the spirit thereof.

The method for exhaled breath analysis according to the present invention can be applied to breath analysis apparatuses capable of determining conveniently in a short period of time, and can be utilized for breath diagnostic apparatuses, stress measuring instruments etc., in the medical field, health care field and the like.

DESCRIPTION OF REFERENCE NUMERALS AND SIGNS 100 breath analysis apparatus
101 vessel
102 injection port
103 outlet port
104 cooling unit
105 electrode zone
106 counter electrode zone
107 chemical substance detection unit
108a, 108b valve
201 water vapor
202a, 202b exhaled breath component
203 exhaled breath
204 condensate
205 charged fine particle
301 mouthpiece
302 trapper for saliva
303 radiating zone
304 connection portion
305 temperature sensor
306 humidity sensor
307 check valve
308 pump
309 control unit
310 display unit
401 condensate
501 Taylor cone
502 condensate
503 charged fine particle
601 Taylor cone
602 charged fine particle
701 second electrode zone
702 condensate
703 aggregate
901 breath cooling condensation apparatus
902 thermal conductor
903 thermoelectric element
904 condensate collecting vessel
905 cap
906 breath leading pipe
907 opening for breath discharge
908 backflow prevention device
909 delivery check valve
910 inflow check valve
911 breath passage tube
912 mouthpiece
913 trapper for saliva
914 heat insulator
915 electric heater
916 flowmeter
917 indicator
1001 X-Y stage
1002 base substance
1003 protein spot
1004 dielectric grid
1005 liquid vessel

What is claimed is:

1. A method for analyzing exhaled breath using a breath analysis apparatus,
    said method comprising:
        providing the breath analysis apparatus which includes a vessel; an injection port of the exhaled breath provided at one end of the vessel; an outlet port of the exhaled breath provided at the other end of the vessel; a cooling unit provided inside the vessel; an electrode zone provided in the vicinity of the cooling unit; a counter electrode zone provided inside the vessel; and a chemical substance detection unit provided in the vicinity of the counter electrode, said exhaled breath contains water vapor and a volatile organic compound,
        injecting the exhaled breath from the injection port into the vessel;
        condensing the exhaled breath on an outer peripheral surface of the electrode zone by cooling the electrode zone with the cooling unit;
        forming charged fine particles from the condensed breath;
        recovering the charged fine particles into the chemical substance detection unit by an electrostatic force; and
        detecting the volatile organic compound included in the charged fine particles recovered.

2. The method for exhaled breath analysis according to claim 1 wherein the volatile organic compound has a molecular weight of no lower than 15 and no higher than 500.

3. The method for exhaled breath analysis according to claim 1 wherein the vessel is closable.

4. The method for exhaled breath analysis according to claim 1 wherein the cooling unit is a thermoelectric element.

5. The method for exhaled breath analysis according to claim 1 wherein the electrode zone is cooled by the cooling unit to a temperature at or below the dew condensation point of the water vapor.

6. The method for exhaled breath analysis according to claim 1 wherein the electrode zone and the cooling unit are in contact either directly or via a thermal conductor.

7. The method for exhaled breath analysis according to claim 1 wherein the electrode zone is a cathode, and the counter electrode zone is an anode.

8. The method for exhaled breath analysis according to claim 1 wherein the charged fine particles comprise water and the exhaled breath component.

9. The method for exhaled breath analysis according to claim 1 wherein the chemical substance detection unit has a mechanism to remove the charge electrified by the charged fine particles.

10. The method for exhaled breath analysis according to claim 1 wherein the chemical substance detection unit is grounded.

11. The method for exhaled breath analysis according to claim 1 wherein the chemical substance detection unit is separable from the vessel.

12. The method for exhaled breath analysis according to claim 1 wherein the step of forming the charged fine particles is carried out by electrostatic atomization.

13. The method for exhaled breath analysis according to claim 1 wherein voltage application between the electrode zone and the counter electrode zone is controlled depending on the electric current flowing between the electrode zone and the counter electrode zone in the step of forming the charged fine particles.

14. The method for exhaled breath analysis according to claim 1 wherein a voltage is applied to the counter electrode toward the chemical substance detection unit in the recovery step.

15. The method for exhaled breath analysis according to claim 14 wherein a thermoelectric element is used for removing the chemical substance by heating the electrode zone.

16. The method for exhaled breath analysis according to claim 1 wherein the electrode zone is heated for removing the chemical substance adhered to the electrode zone.

17. The method for exhaled breath analysis according to claim 1 wherein a thermoelectric element is used for removing a chemical substance by heating the electrode zone.

18. The method for exhaled breath analysis according to claim 1 wherein the chemical substance adhered to the electrode zone is removed with an airflow of a gas other than the exhaled breath.

\* \* \* \* \*